United States Patent
Takebe et al.

(10) Patent No.: US 6,410,699 B1
(45) Date of Patent: Jun. 25, 2002

(54) PROCESS FOR THE PREPARATION OF ISOFLAVONE COMPOUNDS

(75) Inventors: Minoru Takebe; Jitsuo Shiraishi, both of Tokyo-To (JP)

(73) Assignee: Nichimo Kabushiki Kaisha, Tokyo-To (JP)

( * ) Notice: Subject to any disclaimer, the term of this patent is extended or adjusted under 35 U.S.C. 154(b) by 0 days.

(21) Appl. No.: 09/600,045

(22) PCT Filed: Jan. 12, 1999

(86) PCT No.: PCT/JP99/00057

§ 371 (c)(1),
(2), (4) Date: Jul. 11, 2000

(87) PCT Pub. No.: WO99/35138

PCT Pub. Date: Jul. 15, 1999

(30) Foreign Application Priority Data

Jan. 12, 1998 (JP) .............................................. 10-3941

(51) Int. Cl.[7] ........................ C07D 311/40; C07H 17/07
(52) U.S. Cl. ........................................... 536/8; 549/403
(58) Field of Search ................................. 549/401, 403; 536/8

(56) References Cited

U.S. PATENT DOCUMENTS

| 4,366,082 A | * | 12/1982 | Zilliken et al. | 252/404 |
| 4,390,559 A | * | 6/1983 | Zilliken et al. | 426/545 |
| 5,670,632 A | * | 9/1997 | Chaihorsky | 536/8 |
| 5,679,806 A | * | 10/1997 | Zheng et al. | 549/403 |
| 5,702,752 A | * | 12/1997 | Gugger et al. | 426/634 |
| 6,083,978 A | * | 4/2000 | Reed et al. | 514/457 |

OTHER PUBLICATIONS

Ohta et al Agr. Biol. Chem., 43:7, 1415–1419 (1979).*
J. Amer. Chem. Soc., 63 pp. 3273–3276 (1941).*
Patent Abstracts of Japan Publication No. 05170756 Dated Sep. 7, 1993.
Chemical Abstract, vol. 123, Abstract No. 79518 (1995) Kim Beam–Hae, "Constituents of Stem of Lespedeza X Nakaii T. Lee"(Saengyak Hakhoechi, 26 [1] p. 13–17.
Chemical Abstract, vol. 123, Abstract No. 79515 (1995) Kim Beam–Hae, "Constituents of Stem of Lespedeza X Maritima Nakai" (Saengyak Hakhoechi, 26 [1] p. 13–17.

* cited by examiner

*Primary Examiner*—Robert W. Rausuer
*Assistant Examiner*—Kamal A Saeed
(74) *Attorney, Agent, or Firm*—Ladas & Parry

(57) ABSTRACT

A process for preparation of isoflavone compounds, comprising separating isoflavone compounds from a starting material containing isoflavone compounds and/or their precursors by means of extraction, wherein the starting material is subjected to removal of fat prior to the separation of isoflavone compounds by means of extraction.

5 Claims, No Drawings

PROCESS FOR THE PREPARATION OF ISOFLAVONE COMPOUNDS

BACKGROUND OF THE INVENTION

1. Field of the Invention

The present invention relates to a process for preparation of isoflavone compounds from materials that contain isoflavone compounds, especially from those plants that are members of such families as Leguminosae, Rosaceae, Iridaceae, Morus, and *Amarantus inamoenus*. More particularly, the present invention relates to a-process for preparation of, isoflavone compounds, from leguminous plants, especially isoflavone aglycones that are hydrolysates of isoflavone glycosides.

2. Background Art

Isoflavone is represented by the following formula (I):

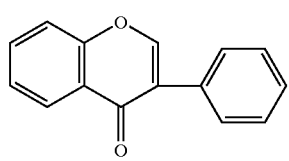

(I)

It has so far been known that isoflavone is naturally present in those plants belonging to Leguminosae, Rosaceae, Iridaceae, Morus and *Amarantus inamoenus*, especially in leguminous plants.

Isoflavone compounds or precursors thereof have the basic isoflavone structure represented by the above formula (I), and various substituents such as alkyl, hydroxyl or alkyloxyl groups.

Isoflavone compounds are represented by the following formula (II):

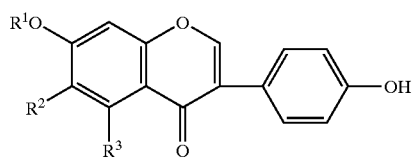

(II)

Representative examples of such isoflavone compounds are shown in Table A.

TABLE A

| $R_1$ | $R_2$ | $R_3$ | Designation |
|---|---|---|---|
| Glucose | H | H | Daidzin |
| Glucose | H | OH | Genistin |
| Glucose | Methoxy | H | Glycitin |
| H | H | H | Daidzein |
| H | H | OH | Genistein |
| H | Methoxy | H | Glycitein |

Among the isoflavone compounds having the above formula (II), those ones whose R, is glucose are referred to as isoflavone glycosides, and hydrolysates of isoflavone glycosides are referred to as isoflavone aglycones.

In recent years, it has become known that isoflavone compounds have estrogen effect, antiestrogen effect, antioxidizing effect, antihemolytic effect, antibacterial effect, anti-lipemic effect, anti-cholesterol effect, anticonvulsant effect, cancered-cell-differentiation-inducing effect, oncogene-blocking effect, carcinostatic effect and other biological activities, and their utility is now attracting public attention.

There are many reports on the pharmacological effects of isoflavone compounds, especially isoflavone aglycones that are hydrolysates of isoflavone glycosides.

For instance, genistein, which is an aglycon formed when glucose contained in genistin, glycoside, is hydrolyzed, has been identified as a substance capable of inhibiting tyrosine kinase (TK inhibitor), tyrosine kinaseibeing essential for the induction of canceration by oncogene, and confirmed to have carcinostatic effect (Akiyama, et al., *Biochemistry*, Vol. 59, No. 9, p. 1016 (1987)).

Further, among isoflavone compounds, genistein particularly shows estrogen effect, and has been confirmed to have therapeutic effect for osteoporosis and immunosuppressive effect.

Postmenopausal osteoporosis is now a great problem for women. The major cause of osteoporosis of this type is decrease in bone density accompanied by excessive metabolic turnover of bones induced by estrogen poyverty.

However, direct administration of estrogen, which is a typical means for treating osteoporosis, has the danger of side-effects to genital organs, causing, for instance, uterine or breast cancer. It is therefore beneficial also from the viewpoint of safety if isoflavone compounds can efficiently be extracted from edible leguminous plants, especially from soybeans, and utilized for health or prophylactic foods.

Since isoflavone compounds have pharmacological effects as mentioned above, there is now an increasing demand for the supply of isoflavone compounds in the medicine and food industries. However, isoflavone compounds are present in natural substances only in small quantities; in particular, isoflavone aglycones are contained in natural substances in extremely small quantities.

For instance, 95% or more of isoflavone compounds present in soybeans, which belong to Leguminosae, are isoflavone glycosides, and isoflavone aglycones are only 5% or less of the isoflavone compounds. For this reason, there is now a demand for a simple process for efficiently recovering isoflavone compounds, especially isoflavone aglycones, from materials containing isoflavone compounds in effective amounts.

To meet this demand, there has been reported, for example, a process for recovering isoflavone compounds from juice of soybeans steamed, using various synthetic absorptive resins (Zenzo KITADA, et al., *The Journal of the Japan Society for Food Industry*, Vol. 33, No. 12, pp. 821–825, December 1986).

This report teaches such a method that juice of soybeans steamed is introduced as a starting material into a column filled with a resin, followed by elution with a water-containing alcohol to recover isoflavone compounds. However, the recovery percentages of the isoflavone compounds obtained are extremely low.

It is possible to obtain isoflavone compounds by the process described in Japanese Patent Laid-Open Publication No. 126186/1987. However, most of the isoflavone compounds obtainable by this method are daidzin and genistin, and isoflavone aglycones, which are isoflavone compounds desired, can be obtained only in low recovery percentages.

Further, there is a report entitled "Shoyu/miso no seizokotei ni okeru Isoflavone oyobi sono haitotai no bunpu-jotai kenkyu-ho (or Method for studying the Distribution of Isoflavone or Its Glycosides in the Process of Production of Soy Sauce/Miso) (1st report)", Kiyoshi KIHARA, *Shoken*, Vol. 16, No. 5, pp. 190–194, 1990.

This report describes that, during fermentation of soybeans to produce soy sauce or miso, isoflavone glycosides are fully hydrolyzed to form isoflavone aglycones. However, this report teaches only a method for qualitatively or quantitatively analyzing isoflavone compounds to show the progress of the hydrolysis of isoflavone glycosides to isoflavone aglycones in each step of production of soy sauce or the like. This method is not suitable at all for the industrial production of isoflavone aglycones.

Japanese Patent Laid-Open Publication No. 170756/1993 describes a method for extracting isoflavone aglycones from isoflavone compounds contained in soy sauce cake or soy sauce oil. To obtain isoflavone aglycones in increased recovery percentages, the fact described in the above-described report that isoflavone glycosides are hydrolyzed to form isoflavone aglycones in the course of the production of soy sauce is applied to this method. However, the recovery percentages of isoflavone aglycones attainable by this method are not yet satisfactorily high.

Japanese Patent Laid-Open Publication No. 258669/1989 discloses a process for producing and recovering isoflavone aglycones, in which isoflavone glycosides are hydrolyzed with the aid of β-glucosidase, one of enzymes which soybeans themselves have. Practically, however, the yields of the isoflavone aglycones produced by this process are low.

The specifications of Japanese Patent Applications No. 32385/1994, No. 179111/1995, No. 26888/1995, No. 88552/1996, No. 83036/1997, etc. which the applicant of the present invention previously filed with the Japanese Patent Office disclose processes for producing concentrated isoflavone compounds containing isoflavone aglycones in large quantities. In these processes, isoflavone glycosides, which are present in legume in large quantities, are hydrolyzed by inoculating grains (soybeans, etc.) with microorganisms such as koji-kin, a fungus belonging to the genus *Aspergillus oryzae*. These are improved or modified processes established on the basis of the fact that isoflavone aglycones are efficiently obtainable from isoflavone glycosides.

Undoubtedly, the aforementioned prior techniques are improved methods useful for separating and recovering isoflavone compounds, especially isoflavone aglycones, from starting materials (methods for increasing the content of isoflavone aglycones by subjecting isoflavone glycosides to hydrolysis by various means being included). However, as far as we know, isoflavone aglycones cannot be obtained in satisfactorily high recovery percentages even by these conventional methods.

In most of the aforementioned prior techniques, especially in techniques represented by the method described in Japanese Patent Laid-Open Publication No. 170756/1993, isoflavone compounds are firstly extracted with an alcohol, washed, and then subjected to removal of fat, using a hydrocarbon or the like; and such a technique that fat is, first of all, fully removed from a starting material has not so far been known at all.

This must be the reason why the recovery of isoflavone glycosides, especially isoflavone aglycones that are hydrolysates of isoflavone glycosides, has not been improved.

SUMMARY OF THE INVENTION

We paid our attention to a method in which fat is, first of all, fully removed from a starting material, and the defatted material is, in the next step, subjected to solvent extraction to prepare isoflavone compounds in high recovery percentages, and finally accomplished the present invention. The present invention is to provide a process for preparation of especially isoflavone aglycones in high recovery percentages. By also taking the utilization of isoflavone aglycones in food products, medicines, etc. into consideration, safety solvents are used in the process of the present invention.

SUMMARY

Namely, the present invention is a process for preparation of isoflavone compounds, comprising separating isoflavone compounds from a starting material containing isoflavone compounds and/or their precursors by means of extraction, wherein the starting material is subjected to removal of fat prior to the separation of the isoflavone compounds by means of extraction.

Typically, the present invention is a process for preparation of isoflavone compounds, comprising the following steps (1), (2), (3) and (4):

(1) removing fat from a starting material containing isoflavone compounds and/or their precursors, and drying the defatted material;

(2) subjecting, to extraction with a solvent, the dried defatted material obtained in the step (1), and concentrating the extract containing isoflavone compounds to dryness;

(3) dissolving, in a solvent, the extract that has been concentrated to dryness in the step (2), diluting this solution with water, and separating from the dilute solution the insoluble matter precipitated; and (4) optionally washing the insoluble matter obtained in the step (3), and drying it to remove the solvent, thereby obtaining isoflavone compounds.

EFFECT

In the process for preparation of isoflavone compounds according to the present invention, especially in the process for producing isoflavone aglycones by the hydrolysis of isoflavone glycosides, fat is removed from the starting material before separating therefrom isoflavone compounds by means of extraction. By doing so, it is possible to successfully solve various problems in the prior art.

It has now been found the following: like in the case of the process in which a starting material containing isoflavone compounds is firstly subjected to extraction with an alcohol (see Japanese Patent Laid-Open Publication No. 170756/1993), when a starting material containing isoflavone compounds (e.g., soy sauce cake) is directly subjected to extraction with a polar solvent, lipids contained in the starting material are also extracted; therefore, even if fat is removed, after the extraction, from the extract by the use of a non-polar solvent (e.g., n-hexane), it is not easy to separate lipids from the isoflavone compounds, and this makes the recovery percentages of isoflavone compounds, especially isoflavone aglycones not so high.

The reason for this is as follows: since isoflavone aglycones are less polar than isoflavone glycos ides for instance, in a thin layer chromatographic analysis of a sample of isoflavone compounds including both isoflavone glycosides and isoflavone aglycones, the change in polarity can well be confirmed if a plurality of liposoluble components are present between the spots of the two compounds), isoflavone aglycones tend to intermingle with liposoluble components, making it difficult to separate isoflavone aglycones from lipids.

On the contrary, the process for preparation of isoflavone compounds according to the present invention is characterized in that fat is, at first, fully removed from a starting material as mentioned above. The process of the present invention is therefore almost free from the above-described problem, and can give the desired substances, isoflavone aglycones, in high recovery percentages.

DETAILED DESCRIPTION OF THE INVENTION

The present invention is to provide a process for preparation of isoflavone compounds, comprising separating isoflavone compounds from a starting material containing isoflavone compounds and/or their precursors by means of extraction, wherein the starting material is subjected to removal of fat prior to the separation of the isoflavone compounds by means of extraction.

Typically, the present invention is a process for preparation of isoflavone compounds, comprising the following steps (1), (2), (3) and (4):

(1) removing fat from a starting material containing isoflavone compounds and/or their precursors, and drying the defatted material;

(2) subjecting, to extraction with a solvent, the dried defatted material obtained in the step (1), and concentrating the extract containing isoflavone compounds to dryness;

(3) dissolving, in a solvent, the extract that has been concentrated to dryness in the step (2), diluting this solution with water, and separating from the dilute solution the insoluble matter precipitated; and (4) optionally washing the insoluble matter obtained in the step (3), and drying it to remove the solvent, thereby obtaining isoflavone compounds.

Process for Preparation Of Isoflavone Compounds
—Starting Material

In the process for preparation of isoflavone compounds according to the present invention, any material can be used as the starting material containing isoflavone compounds and/or their precursors as long as it contains isoflavone compounds in significant amounts. However, if it is intended to use the isoflavone compounds in food products, medicines, etc., it is better that the starting material be of natural origin.

Examples of starting materials of natural origin include plants belonging to such families as Leguminosae, Rosaceae, Iridaceae, Morus and *Amarantus inamoenus*, containing isoflavone compounds in effective amounts; and leguminous plants such as soybeans, azuki beans and other grains are preferred.

In the present invention, not only leguminous plants themselves, but also processed leguminous plants (including, for example, leguminous plants that have been hydrolyzed), and primary or secondary products produced in the course of production of articles, using leguminous plants as starting materials may be used as the starting material either singly or as a mixture of two or more members.

Among leguminous plants, soybeans are preferred. Soybeans can be used irrespective of kind. In addition, there can be used any material selected from processed soybeans, and primary or secondary products produced in the course of production of food products or other articles, using soybeans as starting materials.

Typical examples of these materials include soybeans (irrespective of kind or graincolor), dehulled soybeans, soybean extract, soybean protein isolates, defatted soybeans, soybean protein, soy sauce oil, soy sauce cake, tamari (a kind of soy sauce), miso, mame-miso, natto, fermented soybeans, soybeanmeal, juice of soybeans steamed, and the like.

Those soybeans that have been hydrolyzed to contain isoflavone aglycones in significant amounts are particularly preferred, and typically preferred are soy sauce oil, soy sauce cake, tamari cake, miso, mame-miso, natto, fermented soybeans (including soybeans fermented by microorganisms such as koji-kin, a fungus belonging to the genus *Aspergillus oryzae*), and the like.

It is preferable to fully dehydrate the starting material by drying before use so that it will not be affected by the polarity of a solvent to be used.

The above-described starting materials may be used as the starting material either singly or as a mixture of two or more members. Moreover, the starting material for use in the present invention may be in any form, for example, solid, powder, or minced form, or even in the form of any combination of these forms.

Process for Preparation of Isoflavone Compounds
—Removal of Fat

A conventional method is used to remove fat from the starting material containing isoflavone compounds and/or their precursors.

In the case where a material selected from soybeans (irrespective of kind or grain color), processed soybeans, and primary or secondary products produced in the course of production of food products or other articles, using soybeans as starting materials is used as the starting material, the following methods are typically used for the removal of fat either singly or in combination: a pressing method employing human, animal or water power; a continuous pressing method using an expeller, etc.; a method in which saponification is conducted by the use of sodium hydroxide, etc.; and the like. In the present invention, it is preferable to use a solvent extraction method, which is most frequently used these days.

Through the solvent extraction method, it is possible to fully extract and remove soybean oil and other lipids, which are unnecessary in the process of the invention.

A solvent typically used for this solvent extraction method is a non-polar solvent. Any non-polar solvent can be used as long as it can fully extract unnecessary soybean oil and other lipids contained in the starting material, and as long as it has polarity low enough to avoid the solubilization of isoflavone aglycones.

Typical examples of such non-polar solvents include lower hydrocarbons, petroleum ethers, and other organic solvents, and one of, or two or more of n-hexane, benzene, carbon tetrachloride and the like are generally used.

Particularly preferred in the present invention is n-hexane. n-Hexane does not solubilize isoflavone aglycones.

Moreover, it has been used as an extraction solvent in the food industry, and is thus highly safe.

The above-described method for removing fat is effected by means of extraction under reflux in order to attain increased efficiency of removal of fat. This extraction under reflux is generally conducted at a temperature in the vicinity of the boiling point of n-hexane (approximately 69° C.), typically for about 2 to 5 hours. This length of time varies depending upon the amount of the starting material used.

Process for Preparation of Isoflavone Compounds
—Drying of Defatted Material

A conventional method is used to dry the defatted material that has been obtained by removing fat from the starting material.

Any method can be employed in the present invention as long as it can remove the solvent to such an extent that the solvent will not affect the polarity of a solvent to be used in the next step. The following methods are typically used either singly or in combination: solar drying, (hot) air drying, vacuum drying, through-flow drying, fluidized drying, spray drying, freeze drying, drying under reduced pressure, infrared drying, and high frequency wave drying.

In the present invention, air-drying is preferably used. It is a simple and inexpensive method for removing the solvent that has been used for removing fat from the starting material.

Process for Preparation of Isoflavone Compounds
—Extraction of Isoflavone Compounds A conventional method is used to extract isoflavone compounds from the defatted material that has been dried, and, for this purpose, solvent extraction is typically adopted in the present invention.

Solvent extraction is a method suitable for removing unnecessary components such as proteins, sugars and fibers.

A polar solvent is typically used for this solvent extraction, and any polar solvent can be used as long as it can extract isoflavone compounds, especially isoflavone aglycones, present in the dried defatted material.

Typical examples of polar solvents useful for the solvent extraction include lower esters, water, lower alcohols, lower acetones, and lower fatty acids. Specifically, ethyl acetate, methyl acetate, water, methanol, ethanol, acetone, acetic acid, or the like, or a mixture thereof can be used in the present invention. Of these, particularly preferred in the present invention is ethyl acetate.

Ethyl acetate is a polar solvent particularly suitable for extracting isoflavone aglycones. In addition, it has a low boiling point; and it has been used as an extraction solvent in the food industry, and is thus highly safe.

The above-described solvent extraction is generally conducted at a temperature in the vicinity of the boiling point of ethyl acetate (approximately 77.1° C.), typically for about 2 to 5 hours. This length of time varies depending upon the amount of the starting material used.

After this extraction step, the previously mentioned step of removing fat may optionally be effected to further remove fat.

Process for Preparation of Isoflavone Compounds
—Concentration of Extract to Dryness A conventional method is used to concentrate the extract containing isoflavone compounds to dryness.

Typical examples of methods of concentration include concentration under reduced pressure, concentration by heating, through-flow concentration, freeze concentration, and spray concentration, and these methods may be used either singly or in combination. Concentration under reduced pressure is preferred in the present invention.

This method is advantageous in that, since concentration is conducted under reduced pressure, it is possible to lower the heating temperature and to increase the concentration rate.

It is preferable that the concentration of the extract under reduced pressure be effected in a rotary evaporator or the like to increase the efficiency of concentration by taking into consideration the physical properties of the ethyl acetate (boiling point: approximately 77.1° C.) that has been used in the previous extraction step as a solvent.

Process for Preparation of Isoflavone Compounds
—Dissolution of Extract Concentrated to Dryness and Dilution of Solution with Water (1) Dissolution of Extract Concentrated to Dryness A polar solvent is typically used to dissolve the extract that has been concentrated to dryness. Any polar solvent can be used as long as it can fully dissolve therein isoflavone compounds, polar substances, contained in the extract concentrated to dryness.

Typical examples of polar solvents useful for this dissolution include lower alcohols, water, lower acetones, lower fatty acids, lower esters, and mixtures thereof. Specific examples of these polar solvents include methanol, ethanol, water, acetone, and acetic acid.

In the present invention, lower alcohols such as methanol, ethanol and propanol are preferred, and ethanol is particularly preferred.

Ethanol is a polar solvent suitable for dissolving isoflavone compounds. In addition, it has a low boiling point, and is safe enough for use in food products.

A solvent having a high concentration is preferably used to fully dissolve therein the extract concentrated to dryness. A solvent having a concentration of 95% or more, particularly 99% or more is preferred. The use of a polar solvent having an extremely high concentration is effective to thoroughly dissolve therein isoflavone compounds, which are polar substances.

(2) Dilution of Solution with Water

After dissolving, in the polar solvent, the extract concentrated to dryness, the solution obtained is diluted with water to precipitate, as insoluble matter, isoflavone aglycones whose polarity is slightly lower than that of isoflavone glycosides.

For this dilution, it is preferable to add water in such an amount that impurities having high polarity can be removed and that the purpose of this step, that is, separating isoflavone compounds by insolubilizing them, can be attained.

In the case where the polar solvent that has been used in the above step (1) to dissolve the extract concentrated to dryness is a lower alcohol such as methanol or ethanol, the above purpose can be attained by adding water until the concentration of the alcohol becomes approximately 20%.

Process for Preparation of Isoflavone Compounds
—Separation

A conventional method is used to separate, from the above-obtained dilute solution, the insoluble matter containing considerable amounts of isoflavone compounds whose isoflavone aglycones content is high.

In the present invention, solid-liquid separation is typically used, and a conventional means such as filtration, centrifugal separation, ion exchange, adsorption or concentration is used for the solid-liquid separation.

By conducting liquid-solid separation, it is possible to remove, as soluble matter, lipids and other substances that have relatively high polarity.

Since this soluble matter also contain isoflavone compounds mainly including isoflavone glycosides, it is possible to subject it to extraction to obtain isoflavone glycosides.

Process for Preparation of Isoflavone Compounds
—Optional Washing and Drying The above-obtained insoluble matter is optionally washed to remove unnecessary substances.

The insoluble matter is dried by the same method as that described in the item <Process for Obtaining Isoflavone Compounds —Drying of Defatted Material>, whereby the desired isoflavone compounds are finally obtained.

EXAMPLES

The present invention will now be explained more specifically by referring to the following examples. These examples are given only for a better understanding of the present invention, and not intended to limit the scope of the invention in any way.

Example 1

In accordance with the method described in the specification of the previously mentioned Patent Application filed by the applicant of the present invention, fermented soybean hypocotyl was prepared by inoculating soybean hypocotyl with koji-kin. a fungus belonging to the genus *Aspergillus oryzae*. Isoflavone compounds were separated from this fermented soybean hypocotyl by means of extraction in the following manner.

The fermented soybean hypocotyl, starting material, was ground with a grinding plow into meal of approximately 100 meshes.

n-Hexane was added to this fermented soybean hypocotyl meal in an amount three times the amount of the meal, and extraction was conducted under ref lux for three hours. After the extraction was completed, solid-liquid separation was effected, and the defatted material obtained was dried. The weight of the defatted material dried was approximately 89% of that of the starting material before being subjected to the removal of fat. It was confirmed by thin layer chromatography that the n-hexane after being used for the extraction did not contain isoflavone compounds.

At this point of time, it was found that it was effective to repeat this extraction step two or three more times to thoroughly remove fat.

Subsequently, ethyl acetate was added to the dried defatted fermented soybean hypocotyl, the amount of the former being three times the amount of the latter, and extraction was conducted under reflux for approximately 3 hours. Solid-liquid separation was then conducted, and the ethyl acetate fraction was concentrated in a rotary evaporator under reduced pressure. The extract concentrated to dryness was 2 to 5% of the weight of the starting material.

The following were confirmed at this point of time: to attain an increased recovery percentage, it is preferable to repeat the extraction with ethyl acetate several times; and, in the case where fat has not fully been removed from the starting material, it is preferable to further remove, using n-hexane, fat from the extract concentrated to dryness.

Thereafter, the extract concentrated to dryness was dissolved in a small amount of 99% ethyl alcohol, and this solution was diluted with water until the concentration of the alcohol became approximately 20%, thereby precipitating insoluble matter. This solution was allowed to stand still for a while, and the insoluble matter was then separated by means of solid-liquid separation (filtration using a filter paper), and dried under reduced pressure to obtain isoflavone compounds.

The recovery percentage of the isoflavone compounds was from 40 to 70%.

The isoflavone compounds obtained were introduced into a large-sized column filled with a synthetic absorptive resin (e.g., "Dia-ion HP-20" manufactured by Nippon Rensui Company, Japan) for separation.

By this, the isoflavone compounds were further separated into individual isoflavone compounds, and highly pure daidzin, genistin, daidzein, and genistein were separately obtained in high recovery percentages.

If fat has not fully been removed from the starting material beforehand as in the prior art processes, the efficiency of fractionation of the isoflavone compounds is low even if the synthetic absorptive resin is used. It is therefore considered to be difficult to obtain the isoflavone compounds separately.

The contents of the individual isoflavone compounds in the fermented soybean hypocotyl, starting material, and those of the individual isoflavone compounds in the concentrated isoflavone compounds obtained in accordance with the process of the present invention were respectively measured by the liquid chromatographic method (the method described in J. Agic, *Food Chem.*, Vol. 30, pp. 353–355). The results are as shown in the following Table B.

TABLE B

|  | Starting material (Fermented Soybean Hypocotyl) | Concentrated Isoflavone Compounds |
| --- | --- | --- |
| Daidzin | 0.095% | 1.2% |
| Genistin | 0.043% | 0.5% |
| Daidzein | 0.68% | 43.0% |
| Genistein | 0.12% | 7.0% |

The data in Table B show that the contents of the individual isoflavone compounds in the concentrated isoflavone compounds obtained in accordance with the process of the invention are unusually higher than those of the individual isoflavone compounds in the fermented soybean hypocotyl, starting material. Specifically, the contents of the isoflavone glycosides in the former are as high as about 10 to 13 times the contents of the same in the latter, and the contents of the isoflavone aglycones in the former are about 57 to 64 times the contents of the same in the latter. These results thus demonstrate that isoflavone compounds can simply and efficiently be obtained by the process of the present invention in high recovery percentages.

Example 2

Soy sauce cake that had been produced while producing soy sauce from defatted soybeans by a conventional process was used as the starting material. Isoflavone compounds were recovered from 300 g of this starting material several times in accordance with the process described in Japanese Patent Laid-Open Publication No. 170756/1993.

The recovery percentage of the isoflavone compounds in each time was found to be not higher than approximately 10%.

It was tried to measure, by the same method as in Example 1, the contents of the individual isoflavone compounds in the soy sauce cake, starting material, and those of the individual isoflavone compounds in the concentrated isoflavone compounds obtained. It was however impossible to make the measurement due to the following reasons: the recovery percentages of the individual isoflavone compounds were extremely low, and it was impossible to increase the purity of the individual isoflavone compounds.

In particular, daidzin and genistin were not detected at all.

In the case where the isoflavone compounds were obtained in accordance with the process described in Japanese Patent Laid-Open Publication No. 170756/1993, the recovery percentage of the isoflavone compounds was lower than that of the isoflavone compounds in the process of the present invention; moreover, it was extremely difficult to increase the purity of each isoflavone compound contained in the concentrated isoflavone compounds.

The following were found to be the causes of these unfavorable results: the amount of the defatted material obtained by removing, using n-hexane, fat from the starting material was 290 g; and the percentage of lipids dissolved in the n-hexane was 3% or higher. In addition, it was found that the lipids had extremely high viscosity like tar.

It is therefore assumed in the following way: when the soy sauce cake is directly subjected to extraction with a polar solvent (80% ethanol) as in the process described in Japanese Patent Laid-Open Publication No.170756/1993, the highly viscous lipids are also extracted; the extract is thus brought to such a state that lipids having high polarity and lipids having low polarity are firmly admixed; it is therefore difficult to separate the extract into individual components by the use of a solvent.

The above assumption is based on the following facts: various kinds of lipids are naturally present in soybeans, and they are different in polarity; and, moreover, these lipids are hydrolyzed during the production of soy sauce, so that a large number of components are formed.

Thus, this Example shows that even if fat is removed from the soy sauce cake by the use of n-hexane, it is difficult to separate the isoflavone compounds from lipids.

On the contrary, according to the process for preparation of isoflavone compounds of the present invention, it is possible to smoothly conduct the separation of isoflavone compounds from lipids as shown in Example 1.

As can be understood from the above examples, in the process for preparation of isoflavone compounds according to the present invention, fat is, at first, fully removed from a starting material containing isoflavone compounds and/or their precursors in significant amounts, and the defatted material is then subjected to separation of isoflavone compounds by means of extraction, so that isoflavone compounds, especially isoflavone aglycones, can be obtained in higher recovery percentages than those in prior art processes, as previously mentioned in THE SUMMARY OF THE INVENTION, EXAMPLES, and the like.

Thus, by the use of the process of the present invention, highly concentrated isoflavone compounds, especially isoflavone aglycones, which are excellent in carcinostatic effect, therapeutic effect for osteoporosis, immunosuppressive effect and other medical effects, can be obtained easily and inexpensively from starting materials containing isoflavone compounds and/or their precursors in significant amounts. The isoflavone compounds obtained by the process of the present invention can be supplied in; large quantities as starting materials to the medicine and food industries, in which the supply of isoflavone compounds is now strongly demanded. Further, the isoflavone compounds obtained by the process of the present invention can be used as starting materials for producing individual isoflavone aglycones.

What is claimed is:

1. A process for preparation of an isoflavone aglycone compound, comprising the steps of:
   (1) removing fat from fermented soybeans to form a defatted material and drying the defatted material;
   (2) subjecting the defatted material obtained in step (1) to extraction with a solvent to form an extract containing one or more isoflavone compounds and concentrating the extract to dryness;
   (3) dissolving the extract from in step (2) in a second solvent to form a solution, diluting the solution with water, and separating insoluble matter that precipitates from the solution; and
   (4) washing the insoluble matter obtained in step (3), and drying it to remove the second solvent, thereby obtaining one or more isoflavone aglycone compounds.

2. The process according to claim 1, wherein the fermented soybeans are soybeans fermented by microorganisms.

3. A process for preparation of an isoflavone aglycone compound, comprising the steps of:
   (1) removing fat from fermented soybeans with a non-polar solvent to form a defatted material and drying the defatted material;
   (2) subjecting the defatted material obtained in step (1) to extraction with a polar solvent to form an extract containing one or more isoflavone compounds and concentrating the extract to dryness;
   (3) dissolving, the extract from step (2) in a second polar solvent to form a solution, diluting the solution with water, and separating insoluble matter that precipitates from the solution; and
   (4) washing the insoluble matter obtained in step (3), and drying it to remove the second polar solvent, thereby obtaining one or more isoflavone aglycone compounds.

4. The process according to claim 3, wherein the non-polar solvent for use in step (1) is a lower hydrocarbon, the polar solvent for use in step (2) is a lower ester, and the polar solvent for use in step (3) is a lower alcohol.

5. The process according to claim 3, wherein the non-polar solvent for use in step (1) is n-hexane, the polar solvent for use in step (2) is ethyl acetate, and the polar solvent for use in step (3) is ethanol.

* * * * *